US006449563B1

(12) United States Patent
Dukhin et al.

(10) Patent No.: US 6,449,563 B1
(45) Date of Patent: Sep. 10, 2002

(54) METHOD AND DEVICE FOR DETERMINING PARTICLE SIZE DISTRIBUTION AND ZETA POTENTIAL IN CONCENTRATED DISPERSIONS

(75) Inventors: Andrei Dukhin, Goldens Bridge; Philip J. Goetz, Mt. Kisco, both of NY (US)

(73) Assignee: Dispersion Technology, INC, Mt. Kisco, NY (US)

( * ) Notice: Subject to any disclaimer, the term of this patent is extended or adjusted under 35 U.S.C. 154(b) by 0 days.

(21) Appl. No.: 09/416,662

(22) Filed: Oct. 12, 1999

(51) Int. Cl.[7] ............................................. G01N 30/76
(52) U.S. Cl. ...................................... 702/22; 324/457
(58) Field of Search .................... 702/22; 73/64.42, 73/584, 61.41, 865.5, 64.48, 61.75, 587, 53.01, 606; 324/71.1, 457, 705, 452; 399/27

(56) References Cited

U.S. PATENT DOCUMENTS

| | | | | |
|---|---|---|---|---|
| 4,497,208 A | * | 2/1985 | Oja et al. ...................... 73/584 |
| 4,907,453 A | * | 3/1990 | Marlow et al. ................ 73/584 |
| 5,059,909 A | * | 10/1991 | O'Brien ....................... 324/457 |
| 5,121,629 A | * | 6/1992 | Alba .......................... 73/61.41 |
| 5,245,290 A | * | 9/1993 | Cannon et al. .............. 324/457 |
| 5,293,773 A | * | 3/1994 | Babchin et al. ............. 73/64.48 |
| 5,294,891 A | * | 3/1994 | Saklikar et al. .............. 324/705 |
| 5,528,133 A | * | 6/1996 | Saklikar ..................... 324/71.1 |
| 5,616,872 A | * | 4/1997 | O'Brien ....................... 73/865.5 |
| 5,831,150 A | * | 11/1998 | Sowerby et al. ........... 73/61.75 |
| 6,109,098 A | * | 8/2000 | Dukhin et al. ............. 73/64.42 |

* cited by examiner

*Primary Examiner*—Marc S. Hoff
*Assistant Examiner*—Edward Raymond (57) ABSTRACT

A "coupled phase model" is used to characterize the motion induced by a sound wave of a particle relative to its dispersion medium. A Kuvabara cell model is used to describe the hydrodynamic effects, whereas a Shilov-Zharkikh cell model is used to characterize electrokinetic effects. A different approach for interpreting the experimental data is described in which the electroacoustic sensor is treated as a transmission line with various energy losses due to the reflection and sound attenuation. The experimental output is also expressed as a loss, namely the ratio of the Colloid Vibration Current to the gradient in the acoustic pressure, and is computed by subtracting all other known losses from the total loss of the electroacoustic sensor. These other energy losses can be either calculated or measured directly using reflected pulses.

3 Claims, 7 Drawing Sheets

METHOD AND DEVICE FOR DETERMINING PARTICLE SIZE DISTRIBUTION AND ZETA POTENTIAL IN CONCENTRATED DISPERSIONS

FIELD OF THE INVENTION

The invention relates to the determination of the particle size distribution and zeta potential of particles in a colloidal system.

BACKGROUND OF THE INVENTION

This invention deals with a particular kind of dispersed system (or colloid), which can be described as a collection of small particles immersed in a liquid. These particles can be either solid (suspensions) or liquid (emulsions). Such dispersed systems play an important role in paints, lattices, food products, cements, abrasives, minerals, ceramics, blood, and enumerable other applications.

These systems have a common feature. Because of the small particle size, the total surface area of the particles is large relative to their total volume. Therefore surface related phenomena determine their behavior in many processes. This invention has particular application to dispersed systems where these surface effects are dominant, corresponding to a range of particle size up to about 10 microns. The importance of these surface effects disappears for larger particles.

In particular, this invention deals with concentrated dispersed systems, which are different from dilute systems because of the importance of particle-particle interactions. The boundary between dilute and concentrated systems is somewhat subjective and may vary from 1% vol to 10% vol depending on the measuring technique. We will use the boundary of 2%–5% vol suggested by Hunter in his recent review of electroacoustics. (Hunter, R. J. "Review. Recent developments in the electroacoustic characterization of colloidal suspensions and emulsions", Colloids and Surfaces, 141, 37–65, 1998)

The characterization of such concentrated suspensions and emulsions is important not only for the manufacture, but also the development of new systems with improved properties. There are two basic notions for characterizing these dispersed systems: "particle size distribution" and "zeta potential". Several methods are known for determining these characteristics. Most methods are based on light, for example: microelectrophoresis; light scattering; light diffraction; etc. There is a new alternative method based on ultrasound that is rapidly becoming important. This ultrasound method has a big advantage over traditional light-based techniques because it is able to characterize a concentrated system without dilution. Light-based methods usually require extreme dilution in order to make the sample sufficiently transparent for measurement. This invention deals with improvements of this ultrasound characterization technique.

There are two methods for ultrasound characterization of disperse systems: Acoustics and Electroacoustics. This invention deals only with Electroacoustics. An electroacoustic method applies an acoustic input and measures an electrical response, or conversely applies an electrical input and measures an acoustic response.

This electroacoustic method involves two steps. The first step is to perform an experiment on the disperse system to obtain a set of measured values for certain macroscopic properties such as temperature, pH, Colloid Vibration Current, etc. The second step is an analysis of the measured data to compute the desired microscopic properties such as particle size or $\zeta$ (zeta) potential. Such an analysis requires three tools: a model dispersion, a prediction theory, and an analysis engine.

A "model dispersion" is an attempt to describe the real dispersion in terms of a set of model parameters including, of course, the desired microscopic characteristics. The model, in effect, makes a set of assumptions about the real world in order to simplify the complexity of the dispersion and thereby also simplify the task of developing a suitable prediction theory. For example, most particle size measuring instruments make the assumption that the particles are spherical and therefore a complete geometrical description of the particle is given by a single parameter, its diameter. Obviously such a model would not adequately describe a dispersion of carpet fibers that have a high aspect ratio and any theory based on this over-simplified model might well give incorrect results. The model dispersion may also attempt to limit the complexity of the particle size distribution by assuming that it can be described by certain conventional distribution functions, such as for example a lognormal distribution.

A "prediction theory" consists of a set of equations that describes some of the measured macroscopic properties in terms of these microscopic properties of the model dispersion. For example, a prediction theory for Electroacoustics would attempt to describe a macroscopic property such as the colloid vibration current in terms of such microscopic properties as the particle size distribution and zeta potential.

An "analysis engine" is essentially a set of algorithms, implemented in a computer program, which calculates the desired microscopic properties from the measured macroscopic data using the knowledge contained in the prediction theory. The analysis can be thought of as the opposite or inverse of prediction. Prediction describes some of the measured macroscopic properties in terms of the model dispersion. Analysis, given only the values for some of the model parameters, attempts to calculate the remaining properties by an analysis of the measured data. There are many well-documented approaches to this analysis task.

There are two different approaches to electroacoustic measurements. The first approach employs an electric field to cause the particles to move relative to the liquid. This particle motion generates an ultrasound signal that can be measured. This is the so-called Electrokinetic Sonic Amplitude (ESA) approach. It is described by Oja (U.S. Pat. No. 4,497,208), O'Brien (U.S. Pat. No. 5,059,909), and Cannon (U.S. Pat. No. 5,245,290).

The second approach is the reverse of the first: an ultrasound wave makes the particles move and a resultant electric signal is measured. The electrical signal can be expressed as either a Colloid Vibration Potential (CVP) or a Colloid Vibration Current (CVI), depending on whether one measures the open circuit voltage or the short circuit current between two suitable electrodes. The CVI mode is preferable because it eliminates the need to measure the complex conductivity, which would otherwise be required to calculate the desired $\zeta$ potential. Marlow (U.S. Pat. No. 4,907,453) and Cannon (U.S. Pat. No. 5,245,290) describe this CVI approach.

In principle, the Electroacoustic signal contains information about both particle size and zeta potential. O'Brien suggests using such electroacoustic measurements at multiple frequencies for characterizing both parameters, the so-called "O'Brien method (Column 4). Cannon describes an implementation of this process into a particular device.

There are two main aspects of O'Brien's claims (Column 4, lines 15–22),

"(1) A method for determining particle size and charge from measurement of particle velocity in an alternating electric field"

"(2) A method of obtaining that particle velocity from measurements of the interaction of sound waves and electric fields in the suspension."

From this it becomes clear that the notion of the "particle velocity" or "particle dynamic electrophoretic mobility" (O'Brien, Column 4, lines 30–65) is an essential part of the invention. O'Brien's method [Column 10, line 15, Equation 7] relies heavily on the notion of a "dynamic electrophoretic mobility" $\mu$ and proposes a very simply relationship between $\mu$ and the measured electric current produced by the sound wave $\alpha$ given by:

$$\alpha = \frac{\varphi \Delta \rho}{\rho} \mu \qquad (1)$$

where $\phi$ is the volume fraction of the particles, $\rho$ is a solvent density, and $\Delta\rho$ is the difference between the density of the particles and the density of the solvent.

Equation (1) follows from O'Brien's reciprocal relationship suggested in O'Brien, R. W. "Electro-acoustic Effects in a dilute Suspension of Spherical Particles", J.Fluid Mech., 190, 71–86 (1988)

In point of fact, both theoretical considerations and experimental evidence prove conclusively that Equation 1 is not valid for concentrated systems. From a theoretical viewpoint the equation contradicts the general Onsager principle. Furthermore, the use of O'Brien's equation results in zeta potential errors as large as an order of magnitude when experiments are made with typical concentrated silica or rutile slurries.

Equation 1 purportedly relates an experimentally measured parameter ($\alpha$) with a theoretical parameter ($\mu$) with a coefficient that is deemed independent of frequency. It is assumed that the frequency dependence can be completely incorporated into the "dynamic electrophoretic mobility" term, which is the main reason for introducing this notion into electroacoustic theory. However, this simple Equation 1 does not work. It is impossible to connect $\alpha$ and $\mu$ in a concentrated system using a frequency independent coefficient.

O'Brien's method attempts to account for particle-particle interaction using a Levine "cell model" (Column 8, lines 50–65). (.Levine, S. and Neale, G. H. "The Prediction of Electrokinetic Phenomena within Multiparticle Systems.1.Electrophoresis and Electroosmosis.", J. of Colloid and Interface Sci., 47, 520–532 (1974)). However, it is known that the Levine cell model does not provide a correct transition to the Smoluchowski law (Kruyt, H. R. "Colloid Science", Elsevier: Volume 1, Irreversible systems, 1952), which is known to be valid in concentrated systems.

Historically there have been two different approaches to the development of electroacoustic theory. The first began with works by Enderby and Booth (Booth, F. and Enderby, J. "On Electrical Effects due to Sound Waves in Colloidal Suspensions", Proc. of Amer.Phys.Soc., 208A, 32 (1952) ;Enderby, J. A. "On Electrical Effects Due to Sound Waves in Colloidal Suspensions", Proc.Roy.Soc., London, A207, 329–342 (1951)). They simply tried to solve a system of electrokinetic equations without using any reciprocal thermodynamic relationships. It was very complex because they took into account surface conductivity effects, yet it still was valid only for dilute systems. Marlow and Fairhurst (Marlow, B. J., Fairhurst,D. and Pendse,H. P., "Colloid Vibration Potential and the Electrokinetic Characterization of Concentrated Colloids", Langmuir, 4,3, 611–626 (1983)) continued this approach, but tried to extend it to concentrated systems by introducing the Levine cell model. Unfortunately, this approach leads to somewhat complicated mathematical formulas.

O'Brien later suggested a completely different approach by introducing the term dynamic electrophoretic mobility $\mu$ and deriving the reciprocal relationship expression given in Equation 1, relating this parameter to the measured electroacoustic parameters, such as Colloid Vibration Current (CVI) or Electrokinetic Sonic Amplitude (ESA).

For a time, the introduction of this dynamic electrophoretic mobility appeared to simplify electroacoustic theory by splitting it into two independent problems. The first problem is to develop a theory that relates this dynamic electrophoretic mobility to other properties of the dispersed system. The second problem is to then find a relationship between this dynamic mobility and the measured electroacoustic signal.

However, one important question remained unsolved. In principle, O'Brien's approach and the Enderby-Booth-Marlow-Fairhurst approach (EBMF) should give the same result, but it is not clear if this is the case. The EBMF theory is somewhat more basic. It needs only major well-tested electrokinetic equations. It also can be checked out for Onsager symmetry relationship.

BRIEF SUMMARY OF INVENTION

The applicant describes a new improved theory of electroacoustics that allows one to interpret data over a wide range of concentration up to 50% by volume. We describe a new electroacoustic sensor for making the necessary CVI measurements, electronics for processing this data, additional algorithms for calculating the CVI from the raw data, and means for accurately calibrating the results.

The applicant replaces O'Brien use of dynamic mobility with an improved approach that more accurately relates the parameter a with the properties of the concentrated system. This new theory properly accounts for particle-particle interaction and therefore works even in concentrated systems. Instead of the Levine cell model, the applicant relies on the Shilov-Zharkikh cell model (Shilov, V. N., Zharkih, N. I. and Borkovskaya, Yu. B. "Theory of Nonequilibrium Electrosurface Phenomena in Concentrated Disperse System 1. Application of Nonequilibrium Thermodynamics to Cell Model.", Colloid Journal., 43,3, 434–438 (1981); Dukhin, A. S., Shilov, V. N. and Borkovskaya Yu. "Dynamic Electrophoretic Mobility in Concentrated Dispersed Systems. Cell Model.", Langmuir, accepted), which satisfies Smoluchowski law.

In addition to the basic prediction theory, the applicant also changes the perception about the measurement algorithm. O'Brien's method stresses at several points the necessity of knowing an absolute value of the electroacoustic current ($i_0$) and the absolute value of the pressure difference across the cell (Column 11, lines 25–40). Applicant treats the electroacoustic cell as a transmission line with some energy losses due to the reflection and attenuation. This new approach gives experimental data that is already normalized by pressure. It eliminates the need for absolute values, replacing them with relative numbers using energy conservation law.

The use of a different algorithm for measuring the electroacoustic signal requires very different hardware, as compared to Cannon. The applicant's electroacoustic sensor contains a piezoelectric transducer with quartz delay as the transmitter and an antenna as the receiver. The transmitter and receiver are either mounted separately in a flow-through design or combined to form a probe design that eliminates effects due to colloid attenuation.

DETAILED DESCRIPTION OF INVENTION

The following detailed description of the invention includes improvements in the electroacoustic theory, description of the hardware required to practice the invention including the electroacoustic sensor and electronics, a novel way to obtain the CVI data required to utilize this new theory, a method of precise calibration of the sensor, and experimental verification of the overall approach.

New Electroacoustic Theory

We consider the simpler case of CVI and/or CVP, where the gradient of pressure is the driving force and one measures the resulting electroacoustic signal. We will show that this theory can be also applied to the ESA method, but with some additional complications.

We use a well known "coupled phase model" to describe the particle motion relative to the liquid. The essence of this coupled phase theory [Harker, A. H. and temple, J. A. G., "Velocity and Attenuation of Ultrasound in Suspensions of Particles in Fluids," J. Phys. D.: Appl. Phys., 21, 1576–1588 (1988); Gibson, R. L. and Toksoz, M. N., "Viscous Attenuation of Acoustic Waves In Suspensions," J. Acoust. Soc. Amer., 85, 1925–1934 (1989); Dukhin, A. S. and Goetz, P. J., "Accoustic Spectroscopy for Concentrated Polydisperse Colloids with High Density Contrast," Langmuir, vol. 12, 21, pp. 4987–4997] is to consider the balance of all forces exerted on the particles and on the liquid. In order to specify this balance, one needs to determine a proper inertial frame of reference. This frame of references problem has different implications for the two implementations of electroacoustics.

For the case where sound is the driving force (CVI and/or CVP), a laboratory frame of reference is appropriate, because the wavelength of ultrasound is much shorter than the physical size of the sample chamber. Although particles move at different phases inside of the narrow sound beam, the chamber as an entity remains immobile.

For the reciprocal case, where the electric field is the driving force, the question of an appropriate frame of reference is more complicated. The wavelength of the electric field is much longer and, as a result, all particles in the sample move with the same phase. This motion exerts a certain force on the chamber, and the resultant motion of the chamber depends on the mass of the chamber relative to the mass of the sample. Depending on the construction of the instrument, the appropriate inertial system might be related to the chamber, or to the center of mass, or to some intermediate case depending on the ratio of the mass of the chamber to that of the sample. As a result, the new method can be used for ESA as well, but with an additional multiplier that is dependent on inertial considerations.

For any given element of the dispersed system, there is some force acting on this element due to the sound field. This force is proportional to the gradient of pressure in the sound wave $\nabla P$. This external force is applied to both the particles and the liquid. It is distributed between particles and liquid according to the volume fraction $\phi$. As a result, both particles and liquid move with an acceleration created by the pressure gradient in the sound wave.

In addition, the particles move relative to the liquid, which causes viscous friction forces acting on the particles and liquid.

The Balance of these forces can be presented using the following system of equations written separately for the particles and the liquid:

$$-\varphi \nabla P = \varphi \rho_p \frac{\partial u_p}{\partial t} + \gamma(u_p - u_m) \tag{3}$$

$$-(1-\varphi)\nabla P = (1-\varphi)\rho_m \frac{\partial u_p}{\partial t} - \gamma(u_p - u_m) \tag{4}$$

where $u_m$, and $u_p$ are the velocities of the medium and particles in the laboratory frame of reference, t is time, and $\gamma$ is a friction coefficient. This friction coefficient is proportional to the volume fraction and particle hydrodynamic drag coefficient $\Omega$ as given by:

$$\gamma = \frac{9\eta\varphi\Omega}{2a^2}$$

The drag coefficient $\Omega$ in turn is defined by:

$$F_f = 6\pi\eta\Omega(m_p - u_m)$$

where the frictional force on the particle is $F_f$, $\eta$ is the dynamic viscosity, and a is the particle radius.

This system of equations (3 & 4) is well known in Acoustics. It was utilized in several papers (Harker, A. H. and Temple, J. A. G., "Velocity and Attenuation of Ultrasound in Suspensions of Particles in Fluids", J.Phys.D.:Appl.Phys., 21, 1576–1588 (1988); Gibson, R. L. and Toksoz, M. N., "Viscous Attenuation of Acoustic Waves in Suspensions", J.Acoust.Soc.Amer., 85, 1925–1934 (1989); and, Dukhin, A. S. and Goetz, P. J., "Acoustic Spectroscopy for Concentrated Polydisperse Colloids with High Density Contrast", Langmuir, vol.12, 21, pp. 4987–4997) for calculating sound speed and acoustic attenuation. It is written without any restriction on the volume fraction. It is known that it yields a correct transition to the dilute case.

This system of equations is called the "coupled phase model". The system can be solved in respect to the speed of the relative particle motion. The time and space dependence of the unknown velocities $u_m$ and $u_p$ are presented as a monochromatic waves $A_e^{i(\omega t - lx)}$, where j is a complex unit, and l is a complex wavenumber. As a result, the system of the equations (3 & 4) yields the following relationship between gradient of pressure and relative speed of the particle motion:

$$\gamma(u_p - u_m) = \frac{\varphi(\rho_p - \rho_s)}{\rho_s + i\omega\varphi(1-\varphi)\rho_p \frac{\rho_m}{\gamma}} \nabla P \quad (5)$$

where $\rho_s = \phi\rho_p + (1-\phi)\rho_m$, $\phi$ is volume fraction of the solid particles, and $\rho_p$ and $\rho_m$ are densities of the particle and medium.

Figure 1:
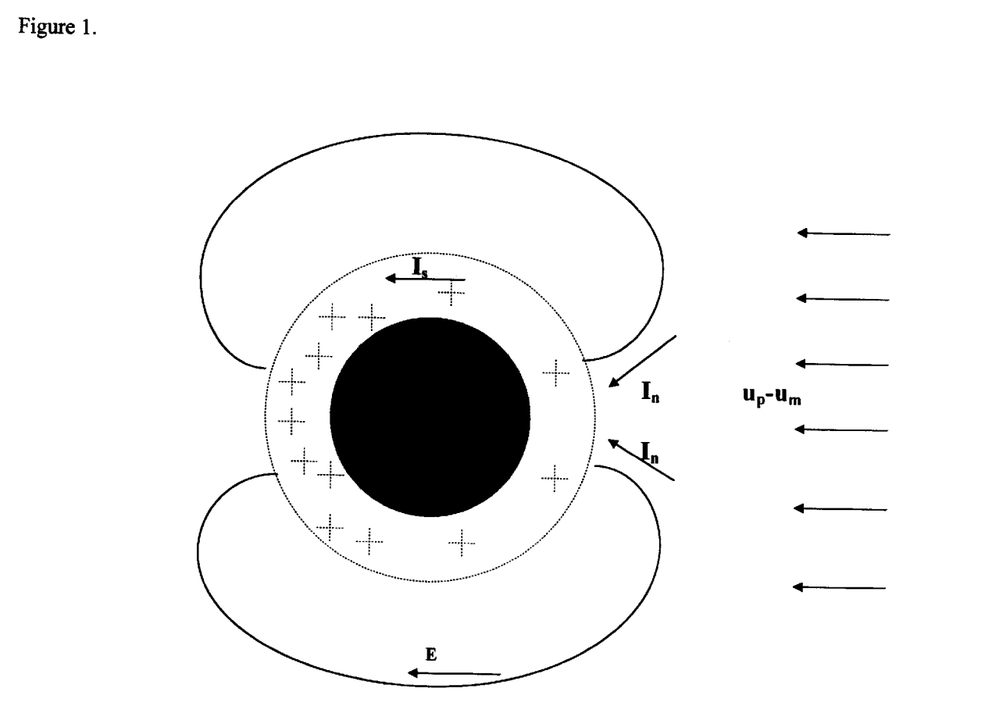
FIG. 1 is a diagram illustrating a particle with a double layer moving relative to the liquid.

The motion of the particles relative to the liquid with the speed $(u_p - u_m)$ disturbs particles double layers and consequently induces electroacoustic phenomena. FIG. 1 illustrates a particle with a double layer moving relative to the liquid. This motion involves ions of the double layer. In this particular case, only positive counter ions of the negatively charged particle are considered. The hydrodynamic surface current $I_s$ reduces the number of the positive ions near the right particle pole and enriches the double layer with extra ions near the left pole. As a result the double layer shifts from the equilbrium Negative surface charge dominates at the right pole, whereas extra positive diffuse charge dominates the left pole, and as a consequence the particle gains an induced dipole moment.

This induced dipole moment generates an electric field, which is usually referred to as the Colloid Vibration Potential (CVP). This field is external to the particle double layer and affects ions in the bulk of the electro-neutral solution beyond the double layer generating an electric current $I_n$. This electric current serves a very important purpose; it compensates for the surface current $I_s$ and makes the entire process self-consistent.

The next step is to add a quantitative description to this simple qualitative picture. In order to do this, the relationship between CVP and $(u_p - u_m)$ is determined using the Shilov-Zharkikh cell model. Marlow explained the advantages of this cell model over the Levine cell model.

Mathematical calculations yield the following expression for Colloid Vibration Current (CVI):

$$CVI = CVP * K_s = \frac{3\varepsilon\varepsilon_0 \zeta K_s}{K_m a} \frac{\varphi}{1-\varphi} \frac{\partial u_\theta}{\sin\theta \partial r}\bigg|_{r=a} \quad (6)$$

where $\epsilon$ and $\epsilon_0$ are dielectric permittivity of the medium and vacuum, $\zeta$ is electrokinetic potential, a is particle radius, $K_m$ and $K_s$ are complex conductivity of the medium and system, $\phi$ is volume fraction, r and $\theta$ are the spherical coordinates associated with the particle center, and $u_r$ and $u_\theta$ are the radial and tangential velocities of the liquid motion relative to the particle.

The next step of the CVI theory is the calculation of the hydrodynamic field, assuming the relative speed of particle-liquid motion is now known and given by expression (5). This is accomplished using the non-stationary Kuvabara cell model [Kuvabara, S "The forces experienced by randomly distributed parallel circular cylinders or spheres in viscous flow at small Reynolds numbers", J.Phys.Soc.Japan, 14,527–532(1959)].

Substituting the drag coefficient into Equation 5 and applying the result to Equation 6, we obtain the following:

$$\frac{CVI}{\nabla P} = \frac{3\varepsilon\varepsilon_0 \zeta K_s \varphi}{2\eta K_m} \frac{(\rho_p - \rho_s)}{\rho_s} G(a, \varphi) \quad (7)$$

where $$G(a, \varphi) = \frac{H + \frac{I}{1-\varphi}}{1.5H - \frac{(1-\varphi)\rho_p - \rho_s}{\rho_s} I}$$

In the case of low surface conductivity and thin double layer

Du<<1

$\chi a$>>1 where $\chi$ is Debye length, ratio of conductivities can be expressed using Maxwell-Wagner theory:

$$\frac{K_s}{K_m} = \frac{1-\varphi}{1+0.5\varphi}$$

We cite below several special functions used in this theory.

$$H(\alpha) = \frac{ih(\alpha)}{2\alpha} - \frac{id\,h(x)}{2dx}\bigg|_{x=\alpha}$$

$h(x) = h_1(x)H_2(\beta) - h_1(\beta)h_2(x)$
$I = I(\beta) - I(\alpha)$
$I(x) = I_1(x) - I_2(x)$ $$I_1(x) = -h_1(\beta)\exp(x(1+i))\left[\frac{3(1-x)}{2\beta^3} + i\left(\frac{x^2}{\beta^3} - \frac{3x}{2\beta^3} - \frac{1}{x}\right)\right]$$

$$I_2(x) = -h_2(\beta)\exp(-x(1+i))\left[\frac{3(1+x)}{2\beta^3} + i\left(\frac{x^2}{\beta^3} + \frac{3x}{2\beta^3} - \frac{1}{x}\right)\right]$$

$$h_1(x) = \frac{\exp(-x)}{x}\left[\frac{x+1}{x}\sin x - \cos x + i\left(\frac{x+1}{x}\cos x + \sin x\right)\right]$$

$$h_2(x) = \frac{\exp(x)}{x}\left[\frac{x-1}{x}\sin x + \cos x + i\left(\frac{1-x}{x}\cos x + \sin x\right)\right]$$

Equation 7 is the new expression for CVI, which this invention proposes for electroacoustic measurements. This expression is valid for thin double layers and for low surface conductivity.

It is instructive to compare our new theory to O'Brien's theory for low frequency. This case is important because it allows us to apply the Onsager reciprocal relationship (Dukhin, S. S. and Derjaguin, B. V. "Electrokinetic Phenomena" in "Surface and Colloid Science", E.Matijevic (Ed.), John Wiley & Sons, NY, v.7 (1974)). These relationships follow from the reversibility of time and link together various kinetic coefficients. These relationships are certainly valid in the stationary case, but much less is known about the validity in the case of an alternating field. Therefore this relationship should only be used in the limiting low frequency case when $\omega \rightarrow 0$ or at least much lower than both the characteristic hydrodynamic and electrodynamic frequencies $\omega_{hd}$ and $\omega_{ed}$ given by:

$$\omega \ll \omega_{hd} = \frac{v}{a^2} \quad (8)$$

-continued $$\omega \ll \omega_{ed} = \frac{K_m}{\varepsilon\varepsilon_0} \quad (9)$$

where $\nu$ is kinematic viscosity, $\nu=\eta/\rho_m$, is dynamic viscosity, a is particle radius, and $K_m$ is conductivity of the medium.

The Onsager relationship provides the following link between CVP, effective pressure gradient that moves liquid relative to the particles $\nabla P_{rel}$, electro-osmotic current $<I>$ and electro-osmotic flow $<V>$:

$$\frac{\langle V \rangle}{\langle I \rangle_{\langle \nabla P \rangle=0}} = \frac{\langle CVP_{\omega \to 0} \rangle}{\langle \nabla P_{rel} \rangle_{\langle I \rangle=0}} \quad (10)$$

In order to use this relationship with respect to CVP, the effective gradient of pressure must first be determined. This parameter can be easily obtained following the "coupled phase model" for characterizing particle motion in the sound field for concentrated system. The total friction force exerted on the particles equals $\gamma(up-u_m)$. This force is a part of the pressure gradient, which moves the particles relative to the liquid. In the extreme case of low frequency Equation 5 leads to the following expression for this effective pressure gradient:

$$\nabla P_{rel}^{\omega \to 0} = \frac{\varphi(\rho_p - \rho_s)}{\rho_s} \nabla P \quad (11)$$

In addition, the expression on the left-hand side of Equation 10 is electrophoretic mobility divided by the complex conductivity of the system $K^*_s$. As a result the following expression for CVI is obtained:

$$CVI_{\omega \to 0} = CVP * K^*_s = \mu \frac{\varphi(\rho_p - \rho_s)}{\rho_s} \nabla P \quad (12)$$

This expression specifies the Colloid Vibration Current at the low frequency limit, in which case $\mu$ corresponds to the stationary case electrophoretic mobility. The Smoluchowski law for electrophoresis is used in the form that is valid in concentrated systems (Dukhin, S. S. and Dedjaguin, B. V., "Electrokinetic Phenomena" in Surface and Colloid Science," E. Matijevic (ed.), John Wiley & Sons, New York, V. 7 (1974)):

$$\mu = \frac{\varepsilon\varepsilon_0 \zeta}{\eta} \frac{K_s}{K_m} = \frac{\varepsilon\varepsilon_0 \zeta (1-\varphi)}{\eta(1+0.5\varphi)} \quad (13)$$

We also use here the Maxwell-Wagner relationship for conductivities in the dispersion of non-conducting particles with low surface conductivity.

As a result we can see that combination of Onsager reciprocal relationship, "coupled phase model" and Smoluchowski law yields the following expression for low frequency CVI:

$$CVI_{\omega \to 0} = CVP * K^*_s = \mu \frac{\varphi(\rho_p - \rho_s)}{\rho_s} \nabla P \quad (14)$$

This is the low frequency asymptotic for all electroacoustic theories. It is a validity test.

Comparing Equation 7 with Equation 14, we see that our new theory satisfies this low frequency validity test because the function $G=1$ for this low frequency limit.

On the other hand, the O'Brien theory with the Levine cell model at the low frequency limit gives the following expression:

$$\mu = \frac{\varepsilon\varepsilon_0 \zeta}{\eta} \frac{K_s}{K_m} = \frac{\varepsilon\varepsilon_0 \zeta (1-\varphi)}{\eta(1+0.5\varphi)} \quad (15)$$

Comparison of the Equation 15 with Equation 14 yields the following ratio between O'Brien's theory and low frequency asymptotic case:

$$\frac{CVP(\omega=0)}{CVI_{\omega \to 0}} = \frac{(\rho_p - \rho_m)\rho_s}{(\rho_p - \rho_s)\rho_m} = 1 + \frac{\rho_p \varphi}{\rho_m(1-\varphi)} \quad (17)$$

Figure 2:
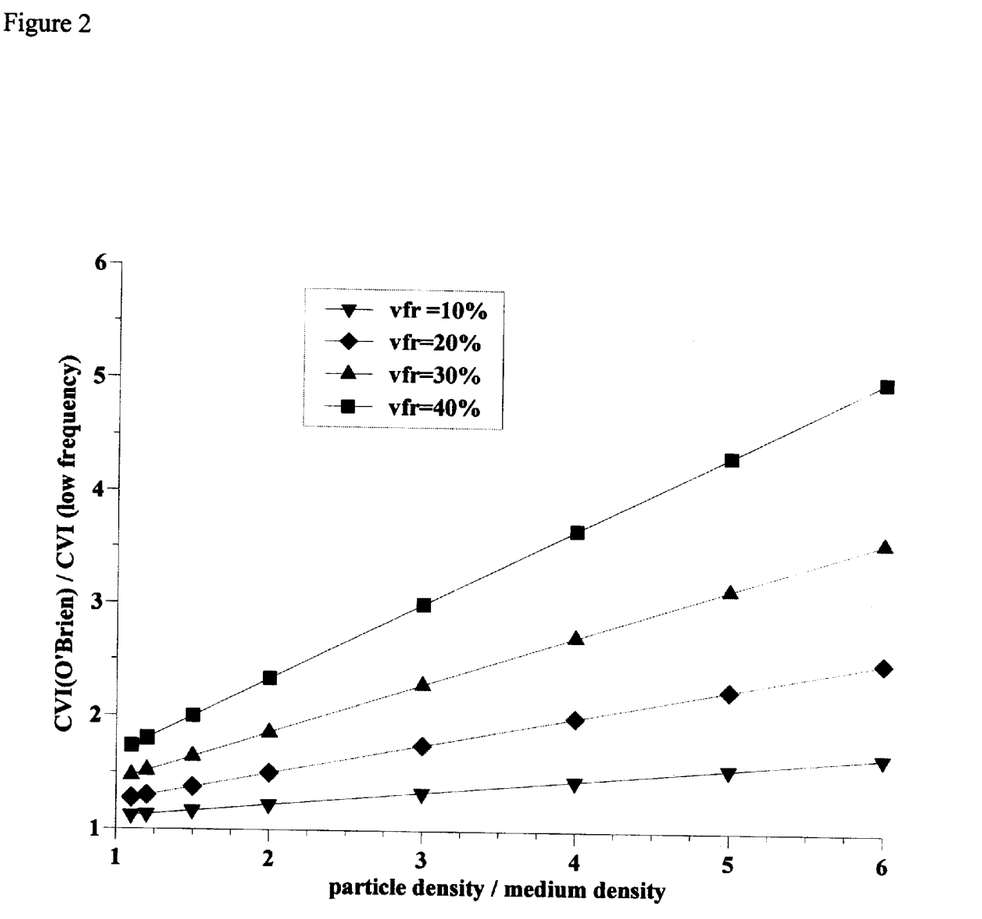
FIG. 2 is a graph illustrating the discrepancy between O'Brien's theory and the new theory at the low frequency asymptotic condition.

FIG. 2 illustrates this discrepancy between O'Brien's theory and the low frequency asymptotic case, as given by Equation 17, is plotted in FIG. 2 as a function of the density contrast between the particles and the suspending medium. Even for a relatively low density contrast samples such as silica particles in water, having a density contrast of 2.0, O'Brien's theory overestimates CVI more than two times for a volume fraction of 40%. For samples such as rutile in water, with a density contrast of approximately 4, the O'Brien theory overestimates CVI by nearly four times at a volume fraction of 40%.

O'Brien's expression for CVI is comprised from the two parts: O'Brien's reciprocal relationship and Levine cell model for dynamic mobility. It is clear that the Levine cell model is not correct. The O'Brien's reciprocal relationship is used with the dynamic electrophoretic mobility derived using the same Shilov-Zharkikh cell model as used in our new theory. This improved O'Brien's theory yields to the following:

$$CVI^* = \frac{3\varepsilon\varepsilon_0 \zeta K_s \varphi}{2\eta K_m} \frac{(\rho_p - \rho_m)}{\rho_m} \frac{H + \frac{I}{1-\varphi}}{15H - \frac{\rho_p - \rho_m}{\rho_m} I} \nabla P \quad (18)$$

Figure 4:
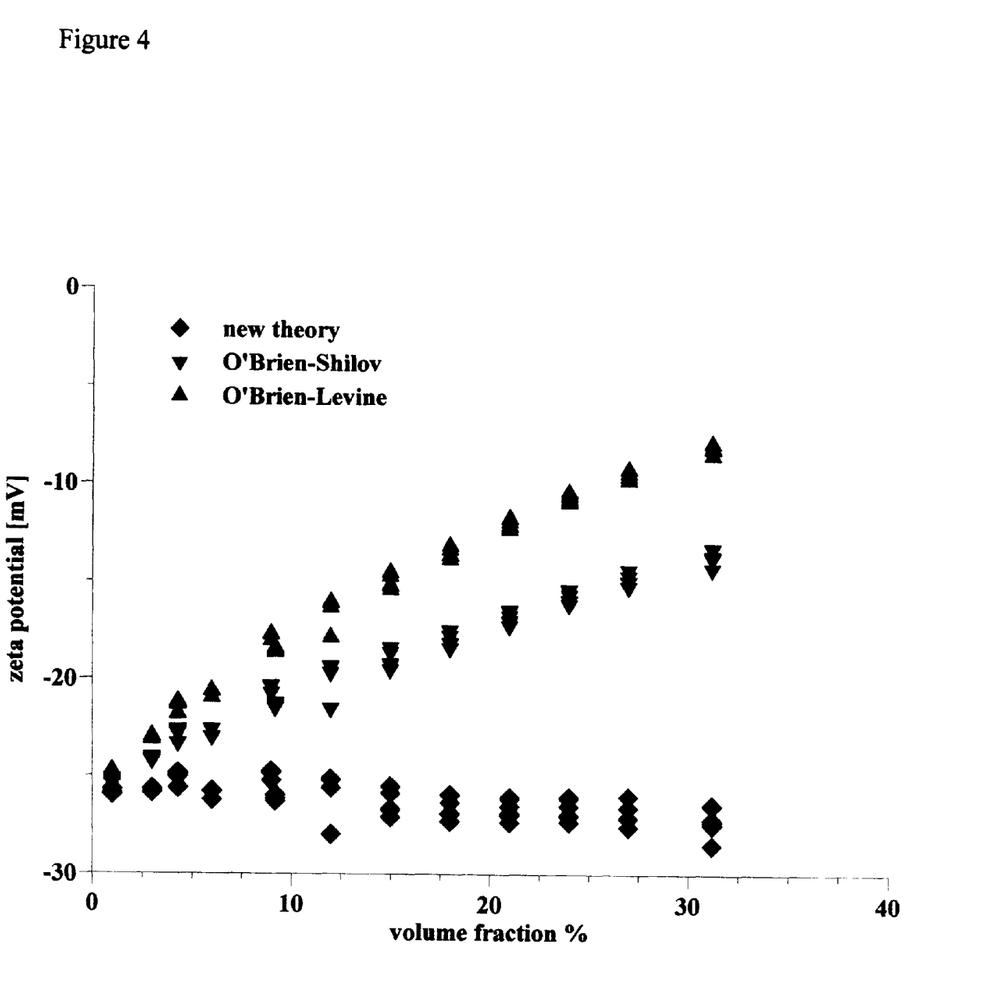
FIG. 4 is a graph showing zeta potential versus volume fraction for silica Ludox calculated using three different methods: the method of this invention, the original O'Brien-Levine method, and the updated O'Brien-Shilov method.

FIG. 4 illustrates differences between the two theories for dispersion with 20% by volume of 1 micron particles. The density of particles is 4 g/cm³, the density of the medium is 1 g/cm³, and the $\xi$-potential is 100 mV. The electroacoustic signal is dimensioned according to the following expression:

$$ElectroacousticSignal = CVI * \frac{2\eta\rho_m}{3\varepsilon\varepsilon_0 \varphi(\rho_p - \rho_m)}$$

It is seen that the difference between the two theories is quite pronounced, which means that not only is the Levine model incorrect, but O'Brien's reciprocal relationship is also wrong. This leads to the conclusion that the "O'Brien's method", as described in U.S. Pat. No. 5,059,909, is not applicable to concentrated systems.

In addition the coupled phase model opens an opportunity to generalize theory for polydisperse system without using superposition assumption. This makes it more general than O'Brien's method, which applies superposition assumption. Our expression for CVI in polydisperse system is the following:

$$\frac{CVI}{\nabla P} = \frac{9\varepsilon\varepsilon_o\zeta(\rho_p - \rho_m)}{4\eta(1+0.5\varphi)} \frac{\sum_{i=1}^{N} \frac{\varphi_i h(\alpha_i)}{j\alpha_i I(\alpha_i)\left(\rho_p - \rho_m\left(\frac{3H}{2I_i}+1\right)\right)}}{1 - \frac{\rho_p}{1-\varphi}\sum_{i=1}^{N} \frac{\varphi_i\left(\frac{3H_i}{2I_i}+1\right)}{\rho_p - \rho_m\left(\frac{3H_i}{2I_i}+1\right)}} \quad (19)$$

This expression can be used for calculating particle size distribution in polydisperse system.

Summarizing all of the above, Applicant replaces O'Brien's method with the new approach for calculating particle size and ξ potential from multiple frequency electroacoustic spectra. In order to extract size information from such electroacoustic spectra the selected frequency range must yield appreciable dispersion in the measured data. Importantly, the previous theory fails to predict the correct range of frequencies for optimum measurement of these CVI spectra O'Brien's method specifies the optimum frequency range with the following expression (Column 6, line 62):

$$v/a^2 < \omega < 4v/a^2 \quad (20)$$

This definition of the optimum frequency range is based on the assumption that critical frequency is independent of the volume fraction of the system. This conclusion apparently follows from the O'Brien-Levine theory for electrophoretic dynamic mobility [Eq.2–6 in U.S. Pat. No. 5,059,909].

Figure 3:
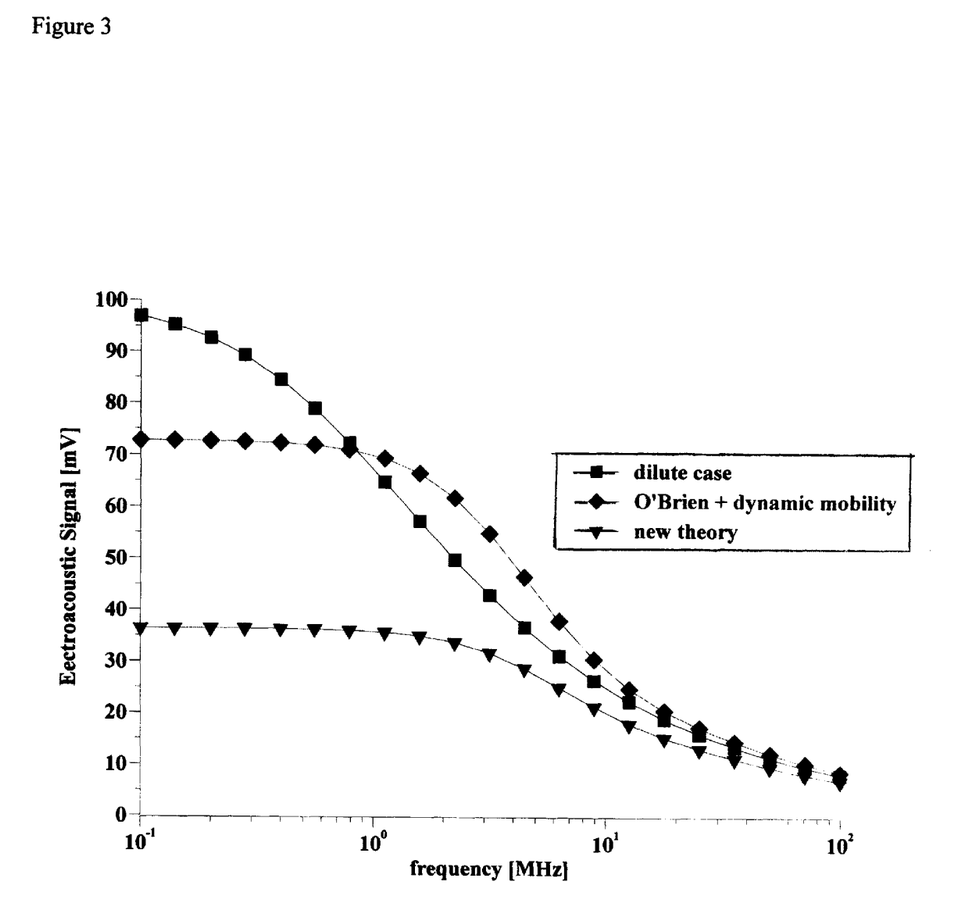
FIG. 3 is a graph depicting frequency dependence of dilute case colloid vibration potential for the O'Brien theory and the method of this invention.

However, the optimum frequency range depends on the volume fraction. For example, the optimum range might change an order of magnitude in going from a dilute to a more concentrated system. The new theory provides a much different and clearer picture of the required frequency range. The new theory predicts that the critical frequency increases with increasing volume fraction. This can be seen from the graphs on FIG. 3. Computer computations show that this frequency shift is about one order of magnitude for volume fraction 40%. This means that the optimum frequency range, if we want to cover volume fractions up to 40%, according to the new theory is:

$$v/a^2 < \omega < 40v/a^2$$

Hardware Description

The proposed electroacoustic spectrometer consists of two parts: a measuring unit and an electronics unit.

Figure 6:
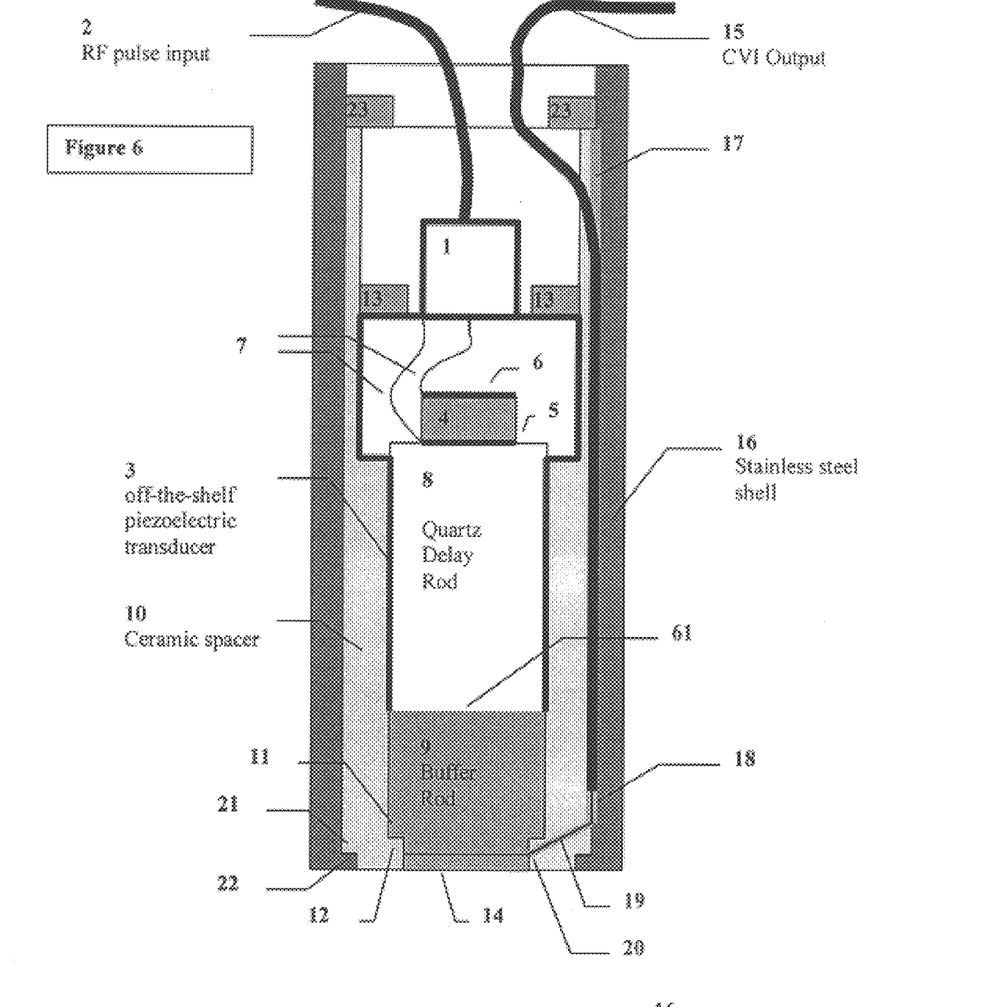
FIG. 6 is a simplified drawing depicting the construction of the electroacoustic probe.

The measuring unit consists primarily of an Electroacoustic Probe, but may optionally include probes for measuring pH and temperature. A drawing illustrating the construction of the probe is shown in FIG. 6.

Figure 7:
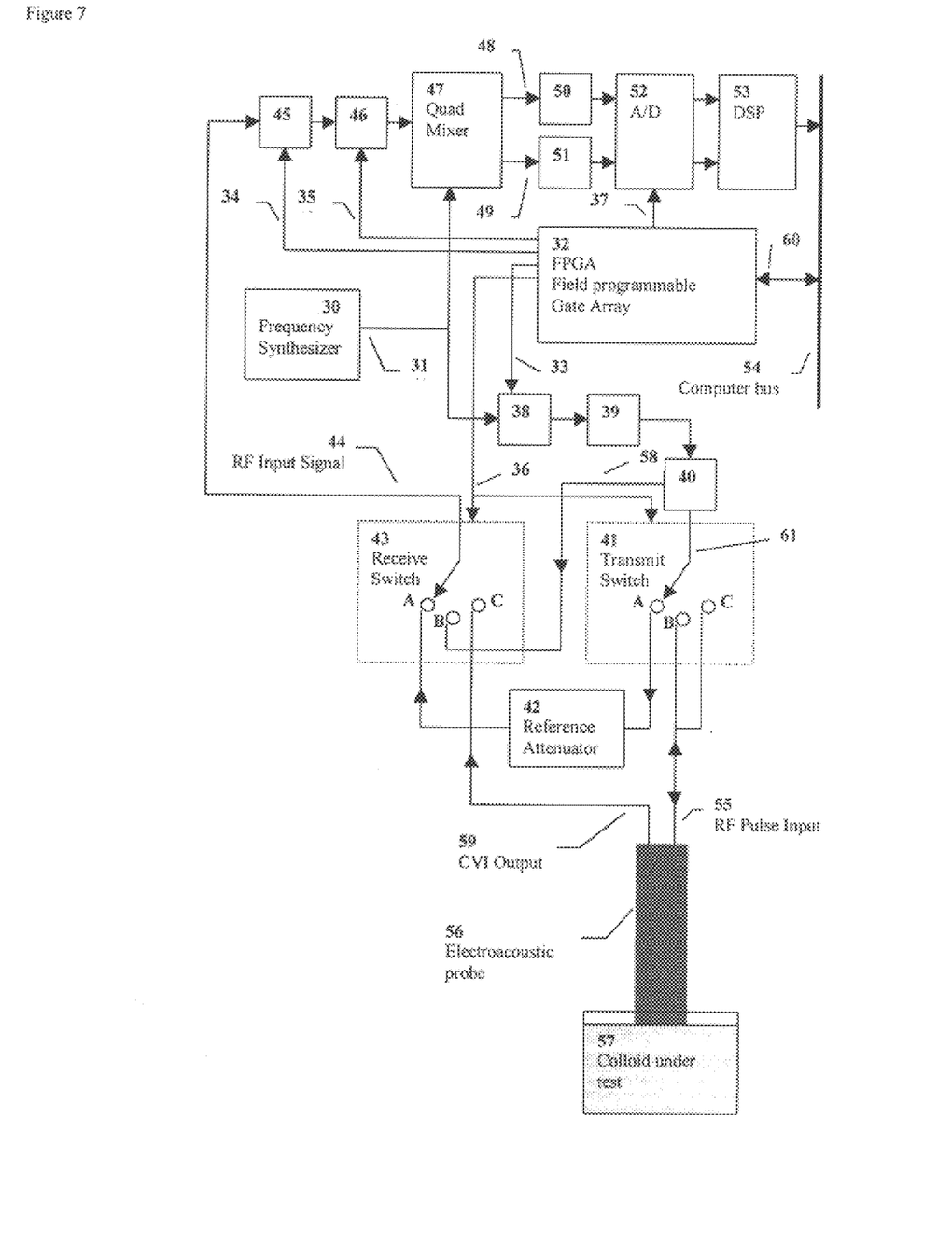
FIG. 7 is a block diagram, showing the probe and the signal processing electronics.

The electronics unit consists of a conventional (IBM clone) computer containing some special purpose signal processing electronics. Windows based software provides a simple graphic interface with user. A block diagram showing the probe and the signal processing electronics is shown in FIG. 7. Optionally, the electronics might also contain conventional data acquisition hardware for measuring parameters such as pH and temperature.

Description of the Electroacoustic Probe

The Electroacoustic probe consists of two parts: a transmitting and a receiving transducer. The transmitting transducer consists of a piezoelectric device to convert a radio frequency (RF) pulse into acoustic energy and a delay rod that launches this acoustic pulse into the slurry after some suitable delay. This acoustic excitation of the slurry causes a very small periodic displacement of the fluid. Although the particles tend to stay at rest because of their inertia, the ionic cloud surrounding charged particles tends to move with the fluid, thereby creating a small oscillating dipole moment. The dipole moment from each particle adds up to create an electric field that can be sensed by the receiving transducer. This receiver in essence consists of a two-element antenna immersed in the sample. The electric field changes the potential of one element with respect to the other. If the impedance of the measuring circuit associated with the antenna is relatively high with respect to the colloid, then the antenna senses an open circuit voltage, which is typically referred to as the colloid vibration potential (CVP). Alternatively, in the preferred configuration, the impedance of the circuitry associated with the antenna circuit is low compared to that of the colloid and therefore the electric field causes a current to flow in the antenna and this short circuit current is referred to as the Colloid Vibration Current (CVI). The probe can be dipped into a test tube for laboratory use, dropped into a storage tank, or inserted into a pipe for online monitoring.

FIG. 6 shows a cross section of the probe. The transmitting portion utilizes an off-the-shelf transducer 3 such as a Panametrics, Inc. Model V356 in conjunction with a mating standard UHF cable connector 1 and input cable 2. This transducer contains a cylindrical piezoelectric device 4 having a front electrode 5 and a back electrode 6 across which an RF pulse can be applied to generate an acoustic pulse. The front and back electrodes of the piezoelectric device are connected to corresponding terminals of the UHF connector by means of internal jumper wires 7 in a manner well known to those skilled in the art of such transducer design. The piezoelectric device in turn is bonded to a quartz delay rod 8 by means of a suitable adhesive. The resonant frequency of the piezoelectric device is selected depending on the frequency range for which electroacoustic data is required. Typically the resonant frequency is selected in the range of 2 to 10 MHz. The quartz delay rod typically has an acoustic delay of about 2.5 usec, which is quite suitable for this purpose. The quartz delay rod is extended by an additional buffer rod 9 having an acoustic impedance that is more closely matched to that of the slurry than is the quartz material. The plastic known commercially as Rexolite has been found to be quite suitable for this purpose. The length of this additional buffer rod is chosen to provide an additional time delay at least as long as the pulse length, typically 2.5 usec. The interface between the delay rod and the buffer rod 62 provides a well-known reflection and transmission coefficient for the incident acoustic pulse since the acoustic impedance of both materials is known precisely.

The acoustic transducer and the additional buffer rod are cemented together and inserted filly into a ceramic spacer 10 till the recess 11 on the buffer rod mates with the shoulder 12 on the ceramic spacer, whereupon it is fastened securely by means of brass retaining ring 13. Vespel, a machine able ceramic, has been found to be quite satisfactory for fabrication of the spacer.

Figure 6A:
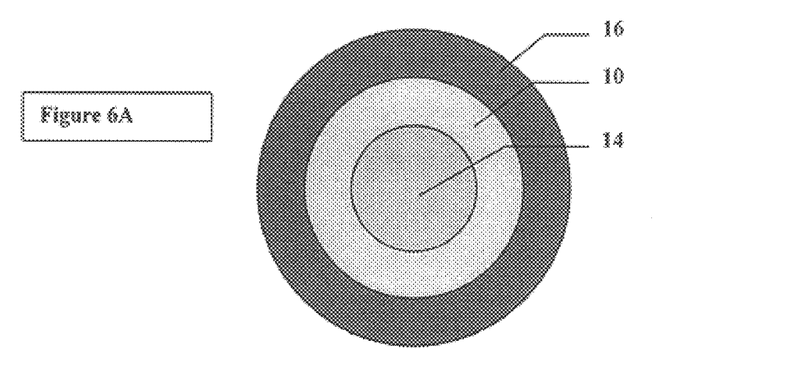

The end of the buffer rod is gold-coated 14 in order to provide an electrode for measuring the electrical response of the colloid to the applied acoustic excitation. This gold coating can be provided either by electroplating the buffer rod or by cementing to it a thin gold foil. Plating has been found to give more reliable performance. A film thickness of 25 microns has been found to be quite suitable. Whether using a plating or foil, the gold coating wraps around the end of the buffer rod approximately 2 millimeters in order to provide a means for making an electrical connection to the gold film electrode. FIG. 6A provides an end view of the probe showing relative location of the gold electrode 14, the ceramic spacer 10, and the stainless steel shell 16.

A coax cable 15 provides the CVI signal and connects to the two electrodes used to receive the colloid vibration signal. The center conductor of the coax connects to the gold electrode and the shield of the coax makes connection to the outer stainless steel shell 16 as will be explained shortly. A groove 17 is provided along substantially the length of the ceramic spacer to provide a path for the coax cable. The outer insulation of the coax is removed from the cable over the length of this groove exposing the outer braid such that it will contact the stainless steel shell. The shield is removed from the final portion 18 of the coax cable in order to expose the center conductor, which is inserted in an access hole 19 in the ceramic spacer such that it makes contact with that part of the gold which wraps around the end of the buffer rod. The coax center conductor is permanently fastened to the gold by means of a small dab of silver filled epoxy 20, or another suitable conductive adhesive.

The ceramic spacer with its internal parts is inserted into the stainless steel shell till a recess 21 at the periphery of the ceramic spacer mates with a flange 22 on the stainless steel shell, whereupon it is fastened securely by means of a retainer ring 23. The stainless steel shell makes electrical contact with the shielded part of the coax contained in the groove. When the probe is immersed in a test sample, the colloid vibration signal between the gold central electrode and the surrounding stainless steel outer housing is thus available at the coax cable output.

Detailed description of the Electronics Unit

The Electronics Unit consists of proprietary signal processing electronics installed in a conventional computer. A block diagram of this electronics is shown in FIG. 7. A frequency synthesizer 30 generates a continuous wave (CW) RF signal 31. A field programmable gate array 32 (FPGA) controlled by the host computer via digital interface 60 generates transmit gate 33, attenuator control 34, receiver gate 35, switch control 36, and A/D strobe command 37. The transmit gate 33 is used by gated amplifier 38 to form a pulsed RF signal from the synthesizer CW signal 31. A power amplifier 39 increases the peak power of this RF pulse to approximately 1 watt. A directional coupler 40 provides a low-loss path for the forward signal from the power amplifier to the transmit switch 41 which then routes this 1 watt RF pulse 61 to one of three channels, labeled A, B, and C according to the FPGA switch control 36.

Channel A is called the reference channel and in this case the output pulse is routed to a precision fixed 40 dB reference attenuator 42. The output of this fixed attenuator is connected to channel A of the Receive Switch 43 where it is then routed to the RF input signal 44. The RF input signal is connected to a wide band RF amplifier 45 having a progrannnable gain set by FPGA attenuator control 34, and thence to a gated amplifier 46 controlled by the FPGA receiver gate 35 which allows only pulses arriving within a predetermined time interval to pass, and thence to a quadrature mixer 47 keyed by the synthesizer output 31 which demodulates the received signal providing analog pulses 48 and 49 proportional to the in-phase and quadrature components of the received RF pulse respectively, thence to separate matched filters 50, 51 for the in-phase and quadrature components, thence to a dual aid converter 52 which digitizes the peak amplitude of these quadrature signals upon an A/D strobe command 37, thence to a digital signal processor (DSP) 53 chip that accumulates data from a large number of such pulses and generates statistical data on a given pulse set, and finally this statistical data is routed to the computer bus 54 so that the data can be analyzed to determine the amplitude and phase of the input signal level 44 for this reference condition. This reference signal level is computed in the following way. The statistical data from the two-channel A/D provides an accurate measure of the in-phase and quadrature components of the received signal at the A/D input. The magnitude is computed by calculating the square root of the sum of the squares of these two signals. The phase is computed from the inverse tangent of the ratio of the in-phase and quadrature components. The magnitude of the RF input signal 44 is then computed by taking into account the overall gain of the RF signal processor as modified by the gain control signal 34.

The use of the reference channel with a known attenuation allows us to measure precisely the attenuation when using the remaining channels B and C. Since we know the input signal level for the 40 dB reference attenuator, any increase or decrease in this signal when using either of the other channels will be proportional to any increase or decrease with respect to this 40 dB reference value.

When the Transmit and Receive Switch are set to Position B, the pulsed RF signal is routed to the RF pulse input 55 of the electroacoustic probe. Inside the probe, this RF pulse is converted to an acoustic pulse and launched down the quartz delay rod. When the pulse meets the interface 62 between the quartz delay rod 8 and the buffer rod 9, a portion of the acoustic signal is reflected back towards the piezoelectric transducer 4 and the remaining portion is transmitted down the buffer rod towards the slurry under test 57. The reflected portion of the pulse is then converted back to an electrical pulse by the piezoelectric device and that pulse is then transmitted back though the directional coupler 40 and the reflected signal 58 is routed to port B of the Receive Switch for processing in a manner identical to that described above. Changes in the value of the received signal, relative to that received for the fixed 40 dB attenuator, allow us to calculate the overall loss for this reflected signal path.

When the Transmit and Receive Switch is set to Position C, the pulsed RF signal is still routed through the circulator to the RF pulse input of the CVI probe, but the Receive Switch connects the CVI Output signal to the RF Input Signal in order to detect the colloid vibration current.

Measurements can be performed for just one frequency or for a chosen set of frequencies from 1 to 100 MHz. Typically the system averages at least 800 pulses, but may accumulate as many as several million pulses if necessary to achieve a satisfactory signal to noise ratio. The number of pulses measured will depend on the properties of colloid. Measurements in low conducting oil based systems may require millions pulses. In principle, this method makes it possible to measure zeta potential in virtually any colloidal system.

Computation of CVI measurement

The measured CVI signal reflects a series of energy losses that are experienced from the point the RF pulse is sent to the probe and the point at which it later returns. These losses include the loss in converting the RF pulse to an acoustic pulse, the reflection losses at the quartz/buffer rod interface, the reflection loss at the buffer rod/colloid interface, and importantly the conversion from an acoustic pulse to a CVI pulse by virtue of the electroacoustic effect which we are trying to characterize. The following paragraphs describe how one calculates the CVI in terms of these effects.

The experimental output of the electroacoustic sensor $S_{exp}$ is the ratio of the output electric pulse from the receiving antenna $I_{out}$ to the intensity of the input RF pulse to the acoustic transmitter $I_{in}$.

$$S_{exp} = \frac{I_{out}}{I_{in}} \quad (21)$$

The intensity of the sound pulse in the delay rod is related to the intensity of this input electric pulse through some constant $C_{tr}$, which is a measure of the transducer efficiency, and any other energy losses to this point:

$$I_{rod} = C_{tr} I_{in} \quad (22)$$

But we are more interested in the sound pressure than the sound intensity. The sound pressure in the rod is given by:

$$P_{rod} = \sqrt{2\rho_{rod} c_{rod} C_{tr} I_{in}} \quad (23)$$

where $\rho_{rod}$ is the density of the rod.

At the receiving transducer, we can define the electric pulse intensity as being proportional to the square of the colloid vibration current generated by the antenna:

$$I_{out} = CVI^2 C_{out} \quad (24)$$

where the constant $C_{ant}$ depends on some geometric factor of the CVI space distribution in the vicinity of the antenna as well as electric properties of the antenna.

Substituting Eq.24 into Eq.21 we obtain the following expression relating CVI with the measured parameter $S_{exp}$:

$$\frac{CVI}{P_{rod}} = \sqrt{S_{exp} / C_{tr} C_{ant} 2\rho_{rod} c_{rod}} \quad (25)$$

But the magnitude of the measured CVI is proportional to the pressure near the antenna surface $P_{ant}$, not in the rod itself The pressure at the antenna is lower than the pressure in the rod $P_{rod}$ for two reasons. First there is a reflection loss at the rod/colloid interface. Second, in the case of the split sensor there is additional attenuation of the acoustic pulse in passing through the colloid in the gap between the transmitting and receiving transducers. There are two ways to take these effects into account. We can measure both the reflection losses and colloid attenuation by sampling the reflected pulses. Alternatively we can calculate these losses from theory. If this second case we can use the following corrections:

$$P_{ant} = P_{rod} \frac{2Z_s}{Z_s + Z_{rod}} \text{EXP}\left(-\frac{\alpha L}{2}\right) \quad (26)$$

where $\alpha$ is the attenuation of the sound intensity expressed in neper/cm, and L is the gap between the transmitting transducer and the receiving antenna in cm. This correction leads to the following expression for CVI:

$$\frac{CVI}{P_{ant}} = \sqrt{S_{exp} / C_{ant} C_{tr} \rho_{rod} c_{rod}} \frac{Z_s + Z_{rod}}{2Z_s} \text{EXP}\left(\frac{\alpha L}{2}\right) \quad (27)$$

The gradient of pressure $\nabla P$ in Eq.7 for CVI equals the gradient of the pressure $P_{ant}$. Using this fact and substituting CVI from the Eq.27 we obtain the following equation relating the properties of the dispersion with the measured parameter $S_{exp}$:

$$\frac{CVI}{\nabla P} = \frac{C_{cal}}{c}\left(1 - i\frac{\alpha c}{2\omega}\right)\sqrt{S_{exp}} \frac{Z_s + Z_{rod}}{2Z_s} \text{EXP}\left(\frac{\alpha L}{2}\right) \quad (28)$$

where c is sound speed in the dispersion.

In the case of polydisperse system we should use Eq.19 instead of the Eq.7.

Attenuation correction is important only in the case when CVI is measured using separate electroacoustic antenna. In the case of electroacoustic probe attenuation is not important because L=0.

This final equation contains an unknown calibration constant $C_{cal}$ that is independent of the properties of the dispersion. This calibration constant can be determined using a colloid with a known zeta potential. For this purpose we use Ludox™, commercially available colloidal silica, which is diluted to 10% wt with $10^{-2}$ mol/l KCl. From independent measurement we have determined that this silica preparation has a $\xi$-potential of −38 mV at pH 9.3.

Expression (28) can be used for calculating $\xi$-potential from a single frequency measurement, or both $\xi$-potential and particle size if the measurement is made for multiple frequencies over an appropriately selected range of frequencies.

Further Details concerning auto Calibration

The calibration constant described above includes two terms: one related primarily to the conversion efficiency of the piezoelectric transducer $C_{tr}$, and one due to the geometry of the CVI antenna $C_{ant}$. As mentioned above, it is possible to calibrate the combined effect of both using a standard colloid of known zeta potential. However, the conversion efficiency of the transducer is frequency dependent whereas the geometric constant for the CVI transducer $C_{ant}$ is not. Furthermore, the transducer efficiency may vary with the age of the transducer as well as ambient temperature. It would be more accurate if there was a means to calibrate the piezoelectric transducer and associated losses separate from the CVI antenna, better yet to do this automatically for each measurement. In this section we describe how to accomplish such automatic transducer calibration.

It is possible to calibrate the transducer efficiency by using the reflected pulse from the quartz/buffer rod interface. This reflected signal originates from the transmitted RF pulse, passes through the circulator 40 with some loss T0, is transformed by the piezoelectric transducer into an acoustic pulse with a corresponding loss T1 and launched down the loss less quartz delay rod 8, whereupon it reflects from the quartz/buffer rod interface with a reflection loss R2, is converted back to an electrical signal in the piezoelectric transducer with the same conversion loss T1 as before, and finally is coupled to the measuring circuit via the directional coupler 40 with a final loss R0. The overall loss L1 from this round trip path is given by:

L1=T0*T1*R2*T1*R0 (27)

Where:
   T0 insertion loss of directional coupler (typically 0.99 or 0.1 db)
   T1 conversion loss of piezoelectric transducer (typically 0.01 or 20 dB at resonance)
   R2 reflection loss at quartz/buffer interface
   R0 return loss in directional coupler (typically 0.01 or 20 dB)

The Transducer Loss T1 is thus given by

T1=Sqr(L1/(T0*R2*R0)) (28)

T0 and R0 are known and independent with frequency. The reflection coefficient R2 can be computed easily from the physical properties of the quartz and Rexolite materials using the relationship:

$$R2=(Z_q+Zr)^2/(4*Zq*Zr) \qquad (29)$$

Where
Zq=acoustic impedance of quartz $=1.55 \times 10^7$
Zr=acoustic impedance of Rexolite$=2.48 \times 10^6$
Substituting these values in Equation 29 we obtain
R2=0.52
Finally, substituting values in Equation 28 we obtain:

$$T1=\sqrt{L1/(0.99*0.52*0.01)}=139\sqrt{L2} \qquad (30)$$

The calibration constant $C_{tr}$ defined earlier reflects the overall loss in intensity between the between the RF pulse and the acoustic pulse at the buffer rod/ colloid interface. Thus we can say that this constant can be expressed as $$C_{tr}=T0*T1*T2 \qquad (31)$$

Where T2 is the transmission coefficient across the quartz/Rexolite interface given by:

T2=1−R2=0.48
Substituting values determined above we obtain:

$$C_{tr}=0.99*139*\sqrt{L2}*0.48=66.1*\sqrt{L2} \qquad (32)$$

Thus the calibration of $C_{tr}$ can be done automatically for each measurement by measuring the loss L2 with the Transmit and Receive Switch set to position B. This calibration is repeated for each frequency of interest.

Experimental Verification of theory

Two different dispersions were used in order to test this new method of particle characterization. The first system was commercially available colloidal silica (Ludox™) having a mean particle size of about 30 nm. Using small particles provides several important simplifications. First of all, the attenuation at low frequency for these small silica particles is negligible and consequently the exponential function in the Equation 26 equals one. Secondly, the sound speed varies less than 2% for weight fractions between 1 and 50%. This eliminates any effects from changes in acoustic impedance. Another important aspect is the absence of any particle size dependence (function G (a)=1). Altogether, this silica system allows us to check experimentally the low frequency theoretical limit without complications produced by sound attenuation or reflection.

The most pronounced effect at low frequency is the dependence of CVI on the volume fraction. Our results are very much different than given by O'Brien's method. This volume fraction dependence can be verified by making zeta potential measurements on a series of equilibrium dilutions. Such an equilibrium dilution series by definition maintains the same chemical properties of the media over the whole range of concentration, thus insuring that the ξ-potential is the same for all volume fractions. Actually, independence of the calculated ξ-potential with volume fraction is perhaps the best confirmation that particular theory is correct.

An equilibrium dilution protocol requires a diluent that is identical to the medium of the given dispersed system. There are two ways to produce such a diluent. One method is separation of the dispersed phase and dispersion medium using either sedimentation or centrifugation. This method does not work for silica Ludox because the particles are too small. The other way is dialysis. Dialysis allows the dispersion to equilibrate with an external solution over some period of time. We used regenerated cellulose tubular membrane Cell*Sept4 with pore size 12,000–14,000 Dalton. The external solution was KCL $10^{-1}$ mol/l with the pH adjusted to 9.5 using hydrochloric acid. The membrane was filled with silica Ludox and placed inside of the KCl solution, which was continuously mixed with magnetic stirrer. Two samples were made at the same time in order to check reproducibility.

Before starting dilution, the weight fraction of the silica Ludox was again checked, using a pyncnometer. There was concern of losing silica particles through the membrane pores into the solution. Weight fraction remained unchanged, which means that pores were too small for silica particles.

There were two sets of 50% silica with corresponding equilibrium solution. It created two ways of checking dilution. One set was used for diluting from the high weight fraction down. This was done by adding solution to the dispersed system. The opposite procedure was used with the other sample. A dispersed system was added to the solution.

We made CVI measurements for the each volume fraction point and then calculated ξ-potential using three separate methods: the O'Brien method with the Levine cell model, O'Brien's method corrected instead with the Shilov-Zharkikh cell model, and finally our new method. The results are shown on FIG. 4. The original O'Brien method yields the largest variation in ξ-potential, whereas our new method is dramatically better yielding a virtually constant ξ-potential over the complete volume fraction range.

Figure 5:
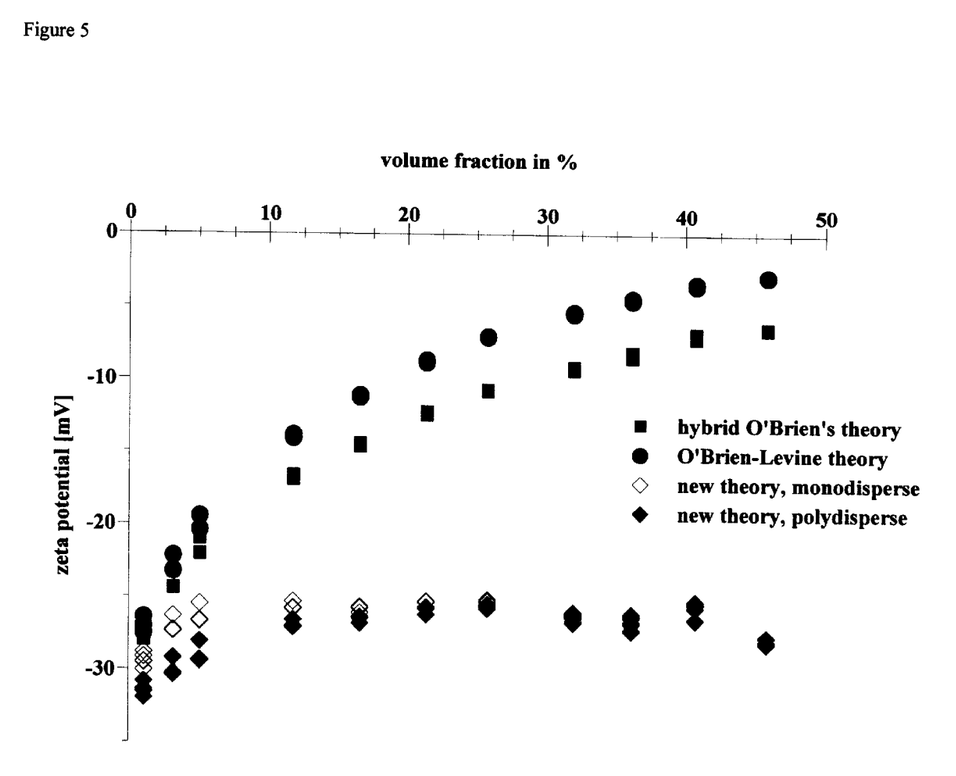
FIG. 5 is a graph showing zeta potential versus volume fraction for rutile R-746 (Dupont) calculated using four different methods: the method of this invention assuming monodisperse system, the method of this invention assuming polydisperse system, the original O'Brien-Levine method, and the updated O'Brien-Shilov method.

The test with the colloidal silica allowed us to test the volume fraction dependence without any complications produced by particle size or attenuation effects. The small size of this colloidal silica insured that the effect of the attenuation on the CVI signal was negligible and that the inertial effects were also negligible. A more difficult test of the theory was done with a concentrated rutile dispersion in which the electroacoustic signal is affected by both attenuation and particle size. A commercially available rutile R-746 produced by Dupont at 76% wt. was used for this purpose. A portion of sample was centrifuged in order to obtain an equilibrium dispersion medium for diluting the concentrated slurry in controlled steps. The results of this experiment are shown in FIG. 5. It is seen again that our method yields much better results, keeping ξ-potential independent of the weight fraction over a wide range.

The invention is described in detail with reference to a particular embodiment, but it should be understood that various other modifications can be effected and still be within the spirit and scope of the invention.

We claim:

1. A device for determining the colloid vibration signals in concentrated dispersions with fluid medium, comprising:
 a piezoelectric device to convert a radio frequency pulse into an acoustic pulse;
 a delay rod, preferably quartz, receiving said acoustic pulse and introducing said pulse into a buffer rod;
 a buffer rod, preferably of plastic material that has an acoustic impedance similar to said concentrated dispersion, receiving said pulse from said delay rod and introducing said pulse into said concentrated dispersion;
 a circular electrode, preferably gold, deposited on the central portion of the end-face of said buffer rod such that it intercepts a significant portion of said acoustic pulse passing into said concentrated dispersion, and being in immediate contact with the colloid eliminates any uncertainty in the amplitude and phase of the CVI signal that would occur if the electrode was located any finite distance from the end of the buffer rod;

an insulated spacer, preferably of some rugged plastic or a machineable ceramic, in which said piezoelectric device, said delay rod, said buffer rod, and said circular electrode are positioned such that only the circular electrode and the end-face of said insulated housing are in contact with said dispersion;

a shell, preferably of stainless steel, in which said insulated spacer is positioned such that the annular end-face of said shell intercepts very little of the acoustic pulse and thus serves essentially as a reference electrode without creating any resonant behavior in the sensor that would occur if this reference electrode was located inside the sound field at some distance into the colloid;

a control unit connected to said piezoelectric device which provides said radio frequency pulses, measures the reflected signals from the interface between said delay rod and said buffer rod, and measures the colloid vibration signals generated between said circular electrode and said reference electrode;

calculating a normalized CVI signal taking into account any variation in the transducer efficiency with frequency or time, by utilizing the reflected signal from the interface between the delay rod and the buffer rod as a reference level pulse.

2. A method of determining particle Zeta potential in concentrated dispersions with fluid medium from a measured colloid vibration current (CVI) comprising the steps of:

using a "coupled phase model" for characterizing the motion of the particles, a Shilov-Zharkikh cell model for electrokinetic effects, and a Kuvabara cell model for hydrodynamic effects.

3. A method of determining the particle size distribution in a polydisperse concentrated dispersions with fluid medium from a measured colloid vibration current (CVI) spectra comprising the steps of:

Selecting a specific set of frequencies over the range defined by $v/a^2<\omega<40v/a^2$ where $v$ is kinematic viscosity, a is a mean particle size, $\omega$ is a frequency;

fitting experimental electroacoustic frequency spectra with theoretical spectra calculated using "coupled phase model" for characterizing motion of particles, Shilov-Zharkikh cell model for electrokinetic effects, Kuvabara cell model for hydrodynamic effects, Maxwell-Wagner-O'Konski theory for conductivity contribution;

and determining at least two moments of the particle size distribution as ajustable parameters of the said fitting procedure.

* * * * *